(12) United States Patent
Itoh

(10) Patent No.: US 8,144,330 B2
(45) Date of Patent: Mar. 27, 2012

(54) EVALUATION METHOD OF FOULING, FOULING EVALUATION APPARATUS, PRODUCTION METHOD OF OPTICAL MEMBER, OPTICAL LAYERED BODY, AND DISPLAY PRODUCT

(75) Inventor: Kiyoshi Itoh, Tokyo (JP)

(73) Assignee: Dai Nippon Printing Co., Ltd., Tokyo (JP)

(*) Notice: Subject to any disclaimer, the term of this patent is extended or adjusted under 35 U.S.C. 154(b) by 429 days.

(21) Appl. No.: 12/440,368

(22) PCT Filed: Sep. 10, 2007

(86) PCT No.: PCT/JP2007/067610
§ 371 (c)(1),
(2), (4) Date: May 1, 2009

(87) PCT Pub. No.: WO2008/029946
PCT Pub. Date: Mar. 13, 2008

(65) Prior Publication Data
US 2010/0118309 A1      May 13, 2010

(30) Foreign Application Priority Data

Sep. 8, 2006 (JP) .................... 2006-244543

(51) Int. Cl.
*G01N 21/94* (2006.01)
*G01N 21/47* (2006.01)
*G02B 1/10* (2006.01)

(52) U.S. Cl. ............ 356/446; 430/270.1; 359/507

(58) Field of Classification Search ............ 356/446, 356/335–339; 250/373, 575; 430/270.1, 430/321
See application file for complete search history.

(56) References Cited

U.S. PATENT DOCUMENTS

| | | | | |
|---|---|---|---|---|
| 3,734,622 A | * | 5/1973 | Adler | 356/338 |
| 5,185,533 A | * | 2/1993 | Banks et al. | 250/575 |
| 5,400,137 A | * | 3/1995 | Winslow et al. | 356/318 |
| 5,406,367 A | * | 4/1995 | Sopori | 356/30 |

(Continued)

FOREIGN PATENT DOCUMENTS

JP      62-011151      1/1987

(Continued)

OTHER PUBLICATIONS

Office Action issued in related Chinese Application No. 200780033180.1 and its full English language translation.

*Primary Examiner* — Sang Nguyen
(74) *Attorney, Agent, or Firm* — Connolly Bove Lodge & Hutz LLP

(57) ABSTRACT

The present invention provides a quantitative evaluation method of fouling of antifouling properties, a fouling evaluation apparatus, and a production method of optical members, which can be applied to various members, and haves high reproducibility and enable to detect a subtle difference between fouling, and an optical layered body having a property of preventing fingerprints from adhering, an anti-contamination property and a degree of recovery from fouling, and a display product including the optical layered body. The present invention pertains to an evaluation method of fouling, wherein light is radiated to a test sample and scattered light reflected off or passing through the test sample is detected to evaluate a degree of fouling of the surface of the test sample.

4 Claims, 2 Drawing Sheets

U.S. PATENT DOCUMENTS

| | | | |
|---|---|---|---|
| 5,825,498 A * | 10/1998 | Thakur et al. | 356/394 |
| 6,441,387 B1 * | 8/2002 | DeSha | 250/573 |
| 6,876,448 B2 * | 4/2005 | Imura et al. | 356/326 |
| 7,592,121 B2 * | 9/2009 | Muramatsu | 430/270.1 |
| 7,659,980 B1 * | 2/2010 | Mitchell et al. | 356/339 |
| 7,719,675 B2 * | 5/2010 | Grygier et al. | 356/300 |
| 2001/0035953 A1 | 11/2001 | Morita et al. | |

FOREIGN PATENT DOCUMENTS

| | | |
|---|---|---|
| JP | 03-044539 | 2/1991 |
| JP | 03151281 A * | 6/1991 |
| JP | 2002-090258 | 3/2002 |
| JP | 2006-046941 | 2/2006 |
| JP | 3745317 | 2/2006 |

* cited by examiner

EVALUATION METHOD OF FOULING, FOULING EVALUATION APPARATUS, PRODUCTION METHOD OF OPTICAL MEMBER, OPTICAL LAYERED BODY, AND DISPLAY PRODUCT

CROSS REFERENCE TO RELATED APPLICATIONS

This application is a national phase of PCT/JP2007/067610, filed on Sep. 10, 2007, which claims priority to JP 2006-244543, filed on Sep. 8, 2006, the entire contents of which are incorporated herein by reference in their entireties.

TECHNICAL FIELD

The present invention relates to an evaluation method of fouling utilizing scattered light passing through or reflected off a test sample, a fouling evaluation apparatus using this method, a production method of optical members, an optical layered body and a display product using the optical layered body.

BACKGROUND ART

An antifouling property is one of performance required in optical members typified by optical films such as an antireflection film for a display, an antireflection film for a touch panel and the like. Specific examples of the points on which prime importance is placed in the antifouling property include a fingerprint adhering property and a fingerprint removing property. That is, in the optical members, since optical properties to be intrinsically exhibited are deteriorated due to fouling through fingerprint-adhering or fouling remaining after removing fingerprints, performance, in which a fingerprint adhering property is low and if the fingerprints adhere, they are easily wiped out, is required.

Further, as an improvement in the antifouling property of the optical member is required increasingly, the reproducibility of the evaluation of the antifouling property itself becomes important. For example, in a patent document 1, an artificial fingerprint liquid for quantitatively evaluating the antifouling property, the fingerprint adhering property or the fingerprint removing property of the surface of an optical disc with high reproducibility.

Patent Document 1: Japanese Patent No. 3745317 (paragraph 0006, 0007)

DISCLOSURE OF THE INVENTION

Problems to be Solved by the Invention

Even though importance is placed on the reproducibility of the evaluation of the antifouling property itself, currently, a method of quantitatively evaluating the antifouling property with high reproducibility is not proposed. For example, an object of the patent document 1 is to improve the reproducibility at a stage of fingerprint-adhering by developing an artificial fingerprint liquid. Quantitative evaluations of the fingerprint adhering property and the fingerprint removing property are performed by measuring the jitter of signals recorded in an optical disc in the patent document 1. This is an evaluation method which can be realized in only the optical disc and this method cannot be widely adopted for optical members to be used for other applications (e.g., optical films such as antireflection films for a display, antireflection film for a touch panel and the like).

Therefore, as evaluations of antifouling properties such as a fingerprint adhering property and a fingerprint removing property, visual sensory evaluations are exclusively carried out at present. However, it is difficult to detect and evaluate a subtle difference between fouling by visual observations and it cannot be necessarily said that the reproducibility is high.

Further, examples of trials to quantify the evaluations of antifouling properties such as the fingerprint adhering property and the fingerprint removing property in the optical members for a display include a method in which an apparatus for evaluating the optical members is used, and evaluation was performed by using changes in haze, contact angles of a water droplet or a solvent, and changes in reflectance. However, light used for measuring the haze or the reflectance is specular reflected light and a light quantity of the specular reflected light is large, and therefore a sensitivity (a S/N ratio as a spectroscope) is low, and this method had a problem that a fine foreign matter such as a fingerprint, which remains after the optical member is fouled with a fingerprint once and then wiped out, cannot be detected. That is, there is a problem that in an apparatus using specular reflected light, a difference between fingerprint-adhering and fingerprint-removing cannot be exactly qualified.

The present invention was made to solve the above-mentioned problems, and it is an object of the present invention to provide an evaluation method of fouling, a fouling evaluation apparatus, and a production method of optical members, which can be applied to various members, have high reproducibility and enable to detect a subtle difference between fouling.

Means for Solving the Problems

To achieve the above object, the present inventor made investigations fundamentally concerning problems of antifouling properties. As a result, human usually perceive the existence of foreign matter, for example, at a display surface through viewing changes in color or luminance of diffusion light of the foreign matter relative to indoor lighting for both transmitted light (transmitted light from inside of a display) and reflected light (reflection of external light to a display surface), and human seldom perceive the existence of foreign matter through viewing changes in specular light due to the existence of foreign matter. Scattered light reflected diffusely by fouling (e.g., fingerprints) adhering to the test sample such as optical members is observed as fouling by human's eyes. The present inventors have noted this fact and found that the degree of fouling of the test sample such as optical members can be evaluated with high reproducibility by detecting the above-mentioned scattered light. These findings have now led to completion of the present invention.

That is, an evaluation method of fouling of the present invention is to evaluate a degree of fouling of the surface of a test sample by radiating light to a test sample and detecting scattered light reflected off or passing through the test sample.

In accordance with the present invention, a quantitative evaluation method of fouling of antifouling properties, which can be applied to test samples, including various optical members, and has high reproducibility and enables to detect a subtle difference between fouling, is provided.

Further, in the evaluation method of fouling of the present invention, the surface of the test sample may be artificially fouled. In accordance with the present invention, it becomes possible to evaluate not only the degree of fouling of the test sample but also the antifouling property (anti-contamination property) of the test sample.

Further, in the evaluation method of fouling of the present invention, the above-mentioned artificial fouling is preferably fouling due to fingerprint-adhering. In the fouling due to fingerprint-adhering, it becomes possible to evaluate the degree of fouling of the test sample and an antifouling property (anti-contamination property) of the test sample with particularly high reproducibility.

Further, in the evaluation method of fouling of the present invention, a degree of recovery from fouling of the surface can be evaluated by cleaning the test sample surface and evaluating the degree of fouling of the test sample again after evaluating the degree of fouling of the surface of the test sample. In accordance with the present invention, it becomes possible to evaluate the degree of recovery from fouling (a degree of recovery of cleanliness) of the test sample.

Further, in the evaluation method of fouling of the present invention, it is preferable to evaluate the degree of fouling of the surface of the test sample based on a L*a*b* color model specified by International Commission on Illumination (CIE). In accordance with the present invention, it becomes possible to obtain highly quantitative and objective evaluation results.

A fouling evaluation apparatus of the present invention includes a setting table of a test sample, a light source for radiating light to the test sample provided on the setting table, an integrating sphere for collecting scattered light reflected off or passing through the test sample, and a scattered light detector for detecting collected scattered light to evaluate a degree of fouling of the surface of the test sample.

In accordance with the present invention, a quantitative evaluation apparatus of fouling of antifouling properties, which can be applied to test samples, including various optical members, and has high reproducibility and enables to detect a subtle difference between fouling, is provided.

A production method of optical members of the present invention includes a step of obtaining an optical member and an inspection step, and in the inspection step, after the surface of the optical member is artificially fouled, light is radiated to the optical member and scattered light reflected off or passing through the optical member is detected to evaluate a degree of fouling of the optical member.

In accordance with the present invention, a quantitative inspection step of antifouling properties, which can be applied to test samples, including various optical members, and has high reproducibility and enables to detect a subtle difference between fouling, is provided.

Further, in the production method of optical members of the present invention, the above-mentioned artificial fouling is preferably fouling due to fingerprint-adhering. In the fouling due to fingerprint-adhering, it becomes possible to evaluate a degree of fouling of the test sample and an antifouling property (anti-contamination property) of the test sample with particularly high reproducibility.

Further, in the production method of optical members of the present invention, in the inspection step, the degree of recovery from fouling of the surface is preferably evaluated by cleaning the surface of the optical member and evaluating the degree of fouling of the optical member again after evaluating the degree of fouling of the surface of the optical member. In accordance with the present invention, an inspection step capable of evaluating the degree of recovery from fouling (a degree of recovery of cleanliness) of the test sample is provided.

Further, in the production method of optical members of the present invention, it is preferable to evaluate the degree of fouling of the surface of the optical member based on a L*a*b* color model specified by International Commission on Illumination (CIE). In accordance with the present invention, it becomes possible to obtain highly quantitative and objective evaluation results.

Further, in the production method of optical members of the present invention, the optical member is preferably an optical film. In accordance with the present invention, an effective production method of optical films which are preferable examples as optical members is provided. Examples of the optical films include not only optical films for a liquid crystal display but also optical films which are applicable to every display such as PDP, CRT and ELD.

Effect of the Invention

In accordance with the present invention, a quantitative evaluation method of fouling of antifouling properties, a fouling evaluation apparatus for carrying out this evaluation method, and a production method of optical members using this evaluation method, which can be applied to test samples, including various optical members, and have high reproducibility and enable to detect a subtle difference between fouling, are provided.

BRIEF DESCRIPTIONS OF THE DRAWINGS

Figure 1:
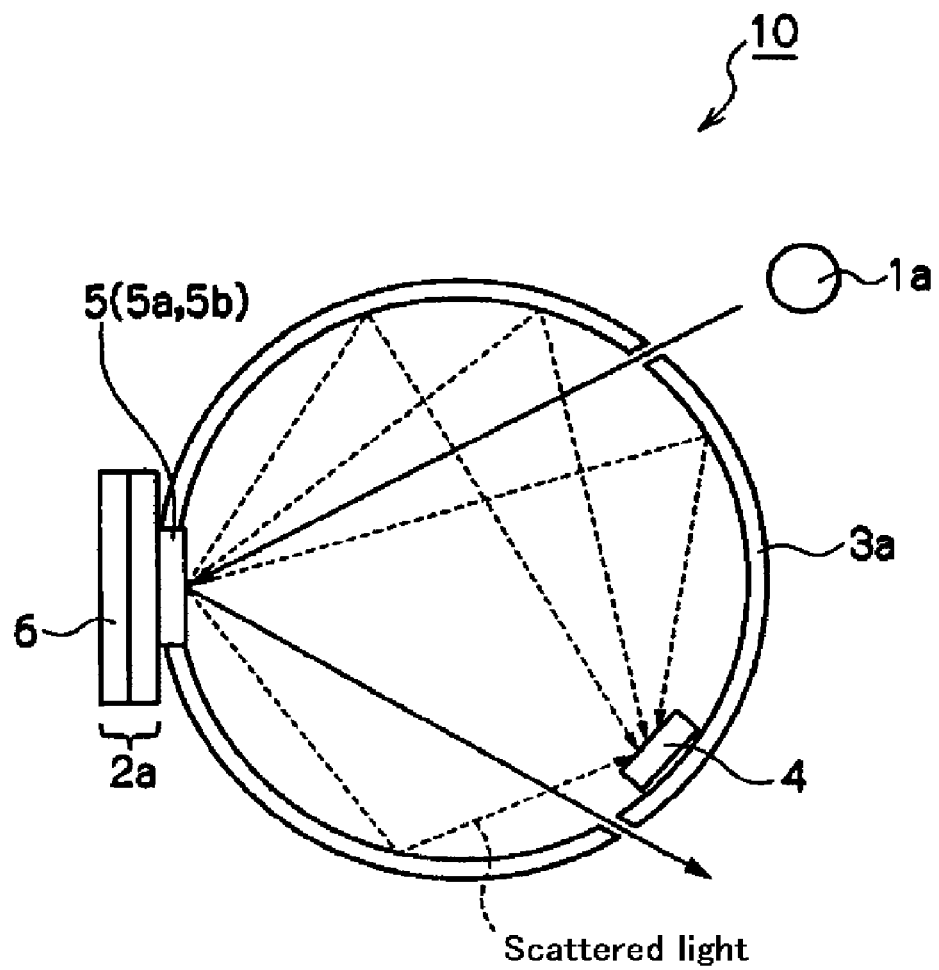
FIG. 1 shows a schematic sectional view of a reflection type fouling evaluation apparatus.

EXPLANATION OF THE NUMERICAL SYMBOLS 1a, 1b light source
2a, 2b setting table
3a, 3b integrating sphere
4 scattered light detector
5, 5a, 5b test sample
6 acrylic plate
10, 11 fouling evaluation apparatus

BEST MODE FOR CARRYING OUT THE INVENTION

Next, embodiments of the present invention will be described in detail, but the present invention is not limited to the following embodiments and various variations can be carried out without departing from its gist.

In the present invention, light is radiated to a test sample and scattered light reflected off or passing through the test sample is detected to evaluate a degree of fouling of the surface of the test sample.

The present invention employs an evaluation technique using the scattered light. By fouling adhering to the surfaces of optical members typified by optical films such as an antireflection film for a display and an antireflection film for a touch panel, reflected light from the surface is reflected diffusely, and scattered light due to the diffuse reflection is viewed with human eyes to be recognized as "fouling (irregularities)". For example, the reason why fingerprints adhering to a display of a mobile phone is annoying is that a reflected light from the display of the mobile phone is reflected diffusely by the adhered fingerprints and the contents displayed in the display become hard-to-view contents. Therefore, by using the scattered light recognized as fouling as an evaluation index of the degree of fouling of the surface of the optical member, it become possible to quantify the degree of fouling.

Hereinafter, specific examples of an evaluation method of fouling and a fouling evaluation apparatus of the present invention will be described referring to drawings. First, the fouling evaluation apparatus will be described.

[Fouling Evaluation Apparatus]

The fouling evaluation apparatus includes a setting table of a test sample, a light source for radiating light to the test sample provided on the setting table, an integrating sphere for collecting scattered light reflected off or passing through the test sample, and a scattered light detector for detecting collected scattered light to evaluate a degree of fouling of the surface of the test sample.

FIG. 1 shows a schematic sectional view of a reflection type fouling evaluation apparatus. A fouling evaluation apparatus 10 in FIG. 1 has a setting table 2a of a test sample 5, a light source 1a for radiating light to the test sample 5 provided on the setting table 2a, an integrating sphere 3a for collecting scattered light reflected off or passing through the test sample 5, and a scattered light detector 4 for detecting collected scattered light to evaluate a degree of fouling of the surface of the test sample 5.

The setting table 2a is used for providing the test sample 5. The test sample 5 is not limited as long as it is a sample requiring evaluating a degree of fouling of its surface. Examples of the test sample 5 include optical members typified by optical films such as an antireflection film for a display and an antireflection film for a touch panel, and optical discs such as a CD, a DVD and a blue laser compatible disc. Since the test sample 5 needs to have a size which can be provided on the setting table 2a, the above-mentioned optical films or optical discs are cut off so as to have the prescribed size as required. In addition, as the test sample 5, a test sample 5a which is fouled or may have been fouled and a test sample 5b which is not fouled are prepared.

By providing the test samples 5a, 5b on the setting table 2a and measuring the test samples 5a, 5b, the degree of fouling of the test sample 5a which is fouled or may have been fouled can be verified using the test sample 5b which is not fouled as a reference (standard). Herein, when the test samples 5a and 5b are a film-like sample, respectively, the test samples are provided without producing wrinkles or sagging in a film. In this time, if a pressure-sensitive adhesive sheet is stuck to the setting table 2a in advance, it is preferable since it becomes easy to fix the test samples 5a, 5b. In addition, in the fouling evaluation apparatus 10, the setting table 2a may be composed of only a black acrylic plate 6.

In providing or fixing the test sample 5a on the setting table 2a, the test sample 5a is positioned by a jig so as to radiate light emitted from the light source 1a to a site of the test sample 5a which is fouled or may have been fouled with reliability.

The light source 1a is used for radiating light to the test sample 5 provided on the setting table 2a. Specifically, the test samples 5a, 5b are fixed to the setting table 2a, and then light is radiated to the test samples 5a, 5b from the light source 1a which is a D65 light source or a C light source of standard light. This standard light is used for color proof or color comparison of printed materials and is preferable for securing evaluation accuracy.

The integrating sphere 3a is used for collecting scattered light reflected off or passing through the test sample 5. As shown in FIG. 1, the integrating sphere 3a is provided with a slit into which light emitted from the light source 1a and radiated to the test samples 5a, 5b enters, and a slit from which light returned by specular reflection at the test samples 5a, 5b exits. Of radiated light, specular reflection light exits out of the integrating sphere 3a through the slit as shown in FIG. 1, and scattered light reflected is repeatedly reflected off an inner wall of the integrating sphere 3a and collected by the scattered light detector 4 (see an arrow shown by the dotted lines in FIG. 1).

The scattered light detector 4 is used for detecting the above collected scattered light to evaluate a degree of fouling of the surface of the test sample 5. As the scattered light detector 4, a spectroscope is generally used. Accordingly, the spectral diffuse reflectance of the test samples 5a, 5b can be measured. As a result of this, chromaticity x, y values and luminance Y values of diffuse reflected light are obtained for the test samples 5a, 5b. Then, using a software or the like, not shown in FIG. 1, the above data is further converted to a*b*L* values, and a color difference ($\Delta E^*ab$) between the test samples 5a and 5b is determined, and whereby the degree of fouling of the test sample 5a which is fouled or may have been fouled can be quantitatively evaluated. Thus, in the present invention, it is preferable to evaluate the degree of fouling of the surface of the test sample 5a based on a L*a*b* color model (L*a*b* colorimetric system) specified by International Commission on Illumination (CIE). By using the L*a*b* color model specified by International Commission on Illumination (CIE), there is an advantage that highly quantitative and objective evaluation results are obtain. All values of x, y, Y and L*a*b* and $\Delta E^*ab$ are values according to CIE.

Figure 3:
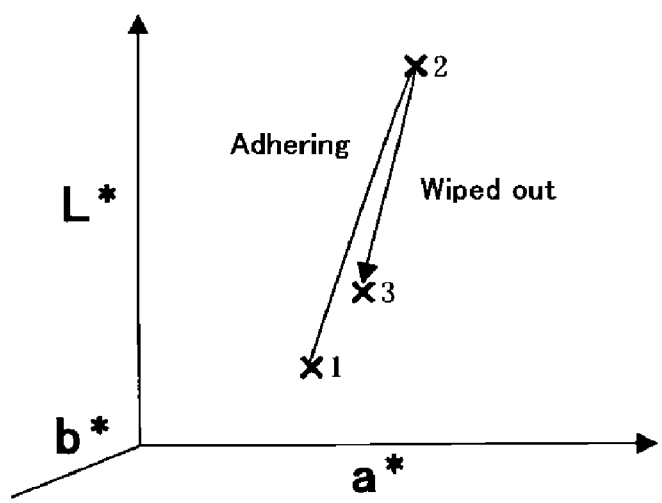
FIG. 3 is a graph showing a relationship of quantitative evaluation of a degree of fouling by $\Delta E^*ab$.

In addition, a graph showing a relationship of quantitative evaluation of a degree of fouling by $\Delta E^*ab$ is shown in FIG. 3. In FIG. 3, X1→X2 shows a case where fouling such as fingerprint-adhering is produced and X2→X3 shows a case where fouling such as fingerprints is cleaned (wiped out). In this time, when a distance between X1 and X2 is small, it indicates that an antifouling property (a property of preventing fingerprints from adhering) is high, and when a distance between X1 and X3 is small, it indicates that a degree of recovery from fouling (a fingerprint removing property) is high.

As the fouling evaluation apparatus 10, for example, a commercially available spectrophotometer equipped with an integrating sphere unit can be used. Therefore, basically, as the light source 1a, the setting table 2a, the integrating sphere 3a, and the scattered light detector 4, those heretofore used in the spectrophotometer can be used as it is. However, in commonly-used spectrophotometers and haze meters, since the integrating spheres are small and a slit solid angle of a detection section is large, it may be hard to detect subtle scattered light produced in light reflected off or light passing through the fouling of the surface of the test sample due to fingerprint-adhering or the like.

In the fouling evaluation apparatus 10, when it is necessary to detect at higher sensitivity because scattered light is subtle, it is preferable to adopt such an apparatus constitution that if the size of window of the integrating sphere in which the test sample 5 is provided is constant, it is preferable to increase the size of the integrating sphere 3a to increase a S/N ratio and decrease the solid angle, and if the size of a integrating sphere 3a is constant, the size of the window of the integrating sphere in which the test sample 5 is provided is reduced to make a quantity of scattered light large. More specifically, it is preferable to employ the integrating sphere 3a having a diameter of 150 mm or more. Further, it is preferable that the size of the window of the integrating sphere in which the test sample is provided is 1 cm×1 cm or less.

Figure 2:
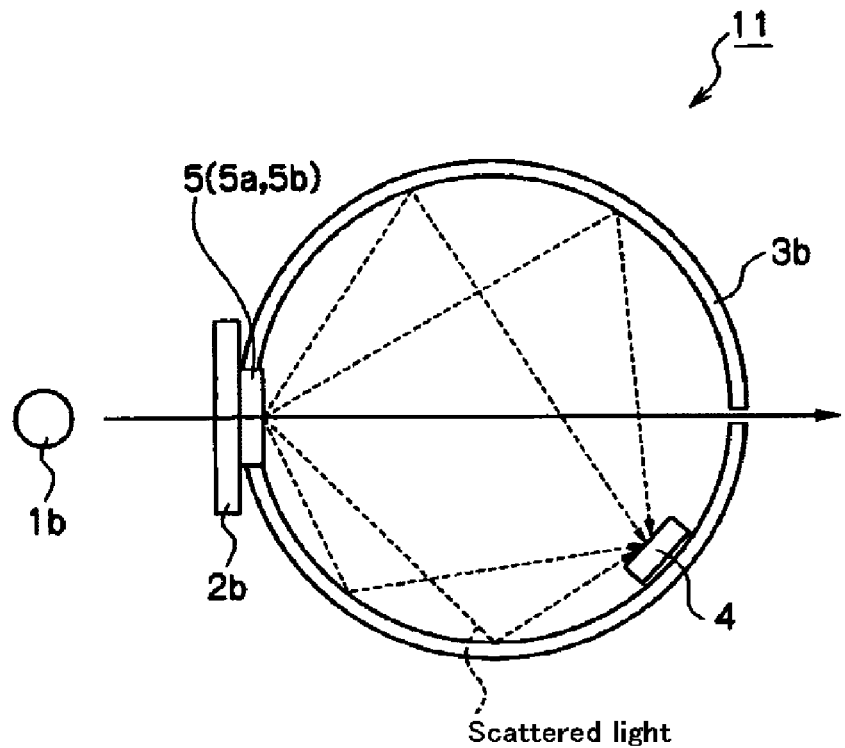
FIG. 2 shows a schematic sectional view of a transmission type fouling evaluation apparatus.

FIG. 2 shows a schematic sectional view of a transmission type fouling evaluation apparatus. A fouling evaluation apparatus 11 in FIG. 2 has a light source 1b, a setting table 2b for providing a test sample 5, an integrating sphere 3b, and a scattered light detector 4. In FIGS. 1 and 2, the same components are given the same reference numerals.

A basic apparatus constitution, operations in measurement, and a measuring principle of the fouling evaluation apparatus 11 may be similar to those of the fouling evaluation apparatus 10. However, the fouling evaluation apparatus 11 is different in the following respects from the fouling evaluation apparatus 10. First, in the fouling evaluation apparatus 10, a black acrylic plate 6 is placed on a back side of the setting table 2a in order to secure the intensity of reflected light from the light source 1a. On the other hand, in the fouling evaluation apparatus 11 utilizing scattered light passing through the test sample 5, the above black acrylic plate is unnecessary. Further, there is a slight difference in a shape between the integrating spheres 3a and 3b based on to a difference of apparatus constitution. Furthermore, in the fouling evaluation apparatus 10, an evaluation of the degree of fouling can be performed whether the test sample 5 has a light transmitting property or not, but in the fouling evaluation apparatus 11, it is necessary that the test sample 5 has a light transmitting property to some extent. However, since the optical member which is a typical example of the test sample commonly has a light transmitting property, the evaluation can be performed in both of the reflection type fouling evaluation apparatus 10 and the transmission type fouling evaluation apparatus 11.

Hereinafter, methods of evaluation of the surface of the test sample in the transmission type fouling evaluation apparatus 11 will be described by way of FIG. 2.

The setting table 2b is used for providing the test sample 5. The test sample 5 may be fixed to the setting table 2b in the same manner as in the reflection type fouling evaluation apparatus 10. Specifically, the fixation may be carried out in a similar manner to the reflection type fouling evaluation apparatus 10 that by providing the test samples 5a, 5b on the setting table 2a, respectively, and measuring the test samples 5a, 5b, the degree of fouling of the test sample 5a which is fouled or may have been fouled can be verified using the test sample 5b which is not fouled as a reference (standard), and that a pressure-sensitive adhesive sheet may be used for the setting table 2b as required.

The light source 1b is used for radiating light to the test sample 5 provided on the setting table 2b. Specifically, the test samples 5a, 5b are fixed to the setting table 2b, and then light is radiated to the test samples 5a, 5b from the light source 1a which is a D65 light source or a C light source of standard light. The radiated light is preferably visible light as with the fouling evaluation apparatus 10. However, light from the light source 1b in the fouling evaluation apparatus 11 is radiated from the back side of the test samples 5a, 5b so as to pass through the test samples 5a, 5b as distinct from the reflection type fouling evaluation apparatus 10.

The integrating sphere 3b is used for collecting scattered light reflected off or passing through the test sample 5. The integrating sphere 3b similar to the integrating sphere 3a used in the fouling evaluation apparatus 10 can be used, and a slit for incident light becomes unnecessary, and on the other hand, a slit for exiting light is placed on an extended line of incident light to the test sample 5. Therefore, the light passing through the test samples 5a, 5b and traveling in a straight line exits out of the integrating sphere 3a through the slit, and the light passing through the test samples 5a, 5b and scattered is repeatedly reflected off an inner wall of the integrating sphere 3b and collected by the scattered light detector 4 (see an arrow shown by the dotted lines in FIG. 2).

The scattered light detector 4 is used for detecting the above collected scattered light to evaluate a degree of fouling of the surface of the test sample 5. As the scattered light detector 4, a spectroscope is generally used as with the fouling evaluation apparatus 10. The measuring method of scattered light may also be the same as in the reflection type fouling evaluation apparatus 10. For example, the color difference of the test samples 5a, 5b may be determined by using the L*a*b* color model specified by International Commission on Illumination (CIE).

[Evaluation Method of Fouling]

In the evaluation method of fouling of the present invention, scattered light reflected off or passing through the test sample is detected to evaluate a degree of fouling of the surface of the test sample. Since a part of the evaluation method of fouling has been referred to in the description of the fouling evaluation apparatus described above, an applicable evaluation of the evaluation method of fouling of the present invention will be described below to avoid duplication of description.

As an applicable evaluation method, a method, in which the surface of the test sample is artificially fouled and the degree of fouling of this surface is evaluated, is preferably employed. By such an applicable evaluation, it becomes possible to evaluate not only the degree of fouling of the test sample but also the antifouling property (anti-contamination property) of the test sample.

By measuring the color difference between the fouled test sample and the reference (test sample not fouled) after various type of test samples are artificially fouled, and comparing the levels of the color difference obtained in each test sample, it becomes possible to relatively evaluate ease of fouling and resistance to fouling (antifouling property) of the test sample precisely. As a result of this, for example, it is possible to obtain an effective evaluation means in development of the test sample (for example, optical member) resistant to fouling.

It is important in evaluating the antifouling property that artificial fouling is performed with high reproducibility. The reason for this is that if an objective degree of fouling varies from the test sample to the test sample when making comparisons of the antifouling property among a plurality of test samples, exact evaluations are hardly made. Specifically, the above-mentioned artificial fouling is preferably fouling due to fingerprint-adhering. Furthermore, in order to inhibit variations between evaluations, it is preferable to adopt a method in which an artificial fingerprint liquid is pressed against the test sample by a certain load to allow the artificial fingerprint liquid to adhere to the test sample rather than a method in which use of human's finger allows the fingerprint to adhere to the test sample. The reason for this is that in use of human's finger, there is a possibility that secreted sebum does not become constant depending on physical condition.

As the artificial fingerprint liquid, for example, a substance introduced in Japanese Patent No. 3745317 can be used. Specific examples of the artificial fingerprint liquid include a pseudo fingerprint liquid containing triolein and fine particles. Then, using a transfer member (for example, a cylindrical indenter) having a prescribed weight, the artificial fingerprint liquid is pressed against the surface of the test sample to allow the artificial fingerprint liquid to adhere to the test sample.

As a further applicable evaluation of the present invention, it is preferable that after evaluating the degree of fouling of the test sample surface, the surface of the test sample is cleaned and the degree of fouling of the test sample is evaluated again. Accordingly, it is possible to evaluate the degree of recovery from fouling (degree of recovery of cleanliness) of the surface.

A test sample in which values of the above-mentioned color difference become small and come closer to a reference after cleaning also enables to evaluate the degree of recovery from fouling (a degree of recovery of cleanliness) of the test sample by its applicable evaluation since this test sample can be said to have a high degree of recovery of cleanliness. If only the degree of fouling of the test sample surface is evaluated, it is possible to evaluate the degree of fouling to some extent based on visual evaluation by human's eyes though the accuracy of evaluation is low. However, it is difficult to visually evaluate the degree of recovery from fouling (a degree of recovery of cleanliness) of the test sample because the cleaned test sample cannot be generally distinguished from a test sample not fouled. On the other hand, since the evaluation method of the present invention can detect subtle scattered light with a high degree of precision, it has an advantage to facilitate making such delicate evaluation as the evaluation of the degree of recovery from fouling (a degree of recovery of cleanliness) of the test sample with high accuracy and with high reproducibility.

The present invention also has an advantage that a test of fouling and a test of a degree of recovery of cleanliness can be separately performed. In the optical member which is one example of the test sample, a substance, being hardly fouled and having a property in which fouling can be clearly wiped out (a degree of recovery of cleanliness is high), is preferably required, but even a substance, being readily fouled but having a property in which fouling can be clearly wiped out (a degree of recovery of cleanliness is high), may be suitable for actual use depending on a use. When such optical members which are "readily fouled but have a property in which fouling can be clearly wiped out (a degree of recovery of cleanliness is high)" are developed, the evaluation method of fouling of the present invention can be preferably employed.

A specific method of cleaning carried out in evaluating the degree of recovery from fouling (degree of recovery of cleanliness) of the test sample is not particularly limited. However, it is important that cleaning of the surface of the test sample is performed with high reproducibility. The reason for this is that if an objective degree of cleaning varies from the test sample to the test sample when making comparisons of the degree of recovery of cleanliness among a plurality of test samples, exact evaluations are hardly made.

When the test sample is an optical member typified by optical films such as an antireflection film for a display and an antireflection film for a touch panel, a method of wiping out the fouling (fouling area) on the structure of the test sample surface by a certain force and at a certain angle with a wiping item such as Kim-Wipe (trademark) is generally employed for cleaning the test sample. If every cleaning can be done at a certain force and a certain angle, cleaning may be carried out manually, and an example of a method of mechanically cleaning include a method of utilizing an abrasion resistance tester. In addition, the antireflection film of the present invention means both antireflection films based on optical interference and antireflection films based on an antiglare property imparted by a surface roughness.

When mechanically cleaning is performed with the abrasion resistance tester, the fouling of the test sample may be wiped out by pressing a wiping item such as Kim-Wipe (trademark) wrapped around an indenter portion of the abrasion resistance tester (for example, an abrasion resistance tester HEIDON TYPE F manufactured by Shinto Scientific Co., Ltd.) against the fouled surface of the test sample under a certain load, and then moving the indenter portion to and fro. Control of the wiping item or the load upon wiping out facilitates cleaning with high reproducibility.

When the fouling of the test sample thus cleaned is evaluated again with the reflection type or the transmission type fouling evaluation apparatus described above, the degree of recovery from fouling (a degree of recovery of cleanliness) of the test sample can be evaluated quantitatively and with high reproducibility.

[Production Method of Optical Member]

The production method of an optical member of the present invention includes a step of obtaining an optical member, and an inspection step in which after the surface of the optical member is artificially fouled, light is radiated to the optical member and scattered light reflected off or passing through the optical member is detected to evaluate a degree of fouling of the optical member. The production method of an optical member of the present invention is a method in which the evaluation method of fouling described above is included in a production step. Consequently, a degree of fouling, anti-contamination property and a degree of recovery from fouling (a degree of recovery of cleanliness) of the surface of the test sample can be evaluated during a production step of the optical member. Therefore, quality control or performance verification of the optical member can be performed, for example, by conducting an inspection step according to the evaluation method of fouling at a final stage of the production step of the optical member.

Examples of the optical members include optical films typified by an antireflection film for a display and an antireflection film for a touch panel. In addition, even substances other than the optical member can be applied to the above-mentioned production method as long as it is an article requiring, for example, evaluation of a degree of fouling of the surface as described examples of the test samples.

Typical examples of the optical members include optical films such as an antireflection film for a display and an antireflection film for a touch panel as described above. There are various forms in optical films. Typical examples of the optical films include optical layered bodies having a constitution in which at least a hard coat layer is formed on a light-transmitting substrate. Further, for example, an antireflection layered body (Anti Reflection product), which has a layer constitution of a light-transmitting substrate/a hard coat layer (it may also serve as a high refractive index layer)/a high refractive index layer (or a medium refractive index layer)/a low refractive index layer, a light-transmitting substrate/a hard coat layer (it may also serve as a high refractive index layer)/a low refractive index layer or the like and is superior in antireflection performance, and an antiglare optical layered body (Anti Glare product), which has a surface roughness at the outermost surface and a layer constitution of a light-transmitting substrate/an antiglare layer (having a hard coat function) can be included. In addition, the antiglare layer may be a monolayer or a multilayer. Further, the low refractive index layer may be formed on the antiglare layer. Furthermore, each layer of the antireflection layered body and the antiglare optical layered body may have various functions such as an antistatic property and the like, or the antireflection layered body and the antiglare optical layered body may have these functions between layers of these optical layered bodies.

(Step of Obtaining Optical Member)

A step of obtaining an optical member will be described below, using a step of obtaining the above-mentioned optical layered bodies as an example.

The step of obtaining the optical layered body commonly has a step of applying a composition for a hard coat layer onto a light-transmitting substrate.

As the light-transmitting substrate, a substrate having smoothness, heat resistance and excellent mechanical strength is preferable.

Examples of materials for forming the light-transmitting substrate include thermoplastic resins such as polyester resins (polyethylene terephthalate, polyethylene naphthalate, etc.), cellulose resins (cellulose triacetate, cellulose diacetate, cellulose acetate butylate, etc.), acrylic resins (polymethyl methacrylate, etc.), polyethersulfone, polysulfone, polypropylene, polymethylpentene, polyvinyl chloride, polyvinyl acetal, polyether ketone, and polycarbonate. Furthermore, examples of materials for forming the light-transmitting substrate also include amorphous olefin polymer (Cyclo-Olefin-Polymer: COP) film having an alicyclic structure. This is a substrate in which norbornene polymer resins, monocyclic olefin polymer resins, cyclic conjugated diene polymer resins, vinyl alicyclic hydrocarbon polymer resins or the like is used. Examples of the amorphous olefin polymer include such as ZEONEX or ZEONOA (norbornene resin) manufactured by ZEON Corporation, SUMILITE (trademark) FS-1700 manufactured by SUMITOMO BAKELITE Co., Ltd., ARTON (modified norbornene resin) manufactured by JSR Corporation, APEL (cyclic olefin copolymer, trademark) manufactured by Mitsui Chemicals, Inc., TOPAS (cyclic olefin copolymer, trade mark) manufactured by Ticona and OPTOREZ OZ-1000 series (alicyclic acrylic resin) manufactured by Hitachi Chemical Co., Ltd.

Further, FV series (low birefringence and low photoelastic coefficient film) manufactured by Asahi Kasei Chemicals Corporation are also preferable as an alternative substrate of triacetyl cellulose.

The thickness of the light-transmitting substrate is commonly 20 μm or more and 300 μm or less, but it may be 300 μm or more and 5000 μm or less in some cases.

The composition for a hard coat layer preferably contains a curable resin.

Examples of the above curable resin include three types of ionizing radiation-curable resins which are resins to be cured with ultraviolet light or electron beams, and a mixture of the ionizing radiation-curable resin and a solvent-drying resin (a resin which forms a coat by only evaporating a solvent previously added in order to adjust a solid content in applying the resin), and a thermosetting resin. The ionizing radiation-curable resins are preferably included. Further, in accordance with a preferred aspect of the present invention, resins containing at least the ionizing radiation-curable resin or the thermosetting resin can be used. In addition, in the present description, the term "resin" is a concept which also comprehends resin components such as a monomer and an oligomer.

Examples of the ionizing radiation-curable resins include compounds having one or two or more unsaturated bonds such as compounds having acrylic functional groups and the like.

Examples of the above compounds having one unsaturated bond include ethyl (meth) acrylate, ethylhexyl (meth) acrylate, styrene, methylstyrene, N-vinylpyrrolidone, and the like.

Further, examples of the compounds having two or more unsaturated bonds include polyfunctional compounds such as trimethylolpropane tri(meth)acrylate, hexanediol (meth) acrylate, tripropylene glycol di(meth)acrylate, diethylene glycol di(meth)acrylate, pentaerythritol tri(meth)acrylate, dipentaerythritol hexa(meth)acrylate, 1,6-hexanediol di(meth)acrylate and neopentyl glycol di(meth)acrylate; and reaction products (for example, a poly(meth)acrylate ester of polyhydric alcohol) of the polyfunctional compound with (meth)acrylate, and the like. In addition, in the present description, "(meth)acrylate" refers to methacrylate and acrylate.

Besides the above-mentioned compound, a polyester resin, a polyether resin, an acrylic resin, an epoxy resin, a urethane resin, an alkyd resin, a spiroacetal resin, a polybutadiene resin, and a polythiol-polyen resin, which have an unsaturated double bond and a relatively low molecular weight, can also be used as the ionizing radiation-curable resin.

When the ionizing radiation-curable resin is used as an ultraviolet-curable resin, it is preferable to use a photopolymerization initiator. Specific examples of the photopolymerization initiator include such as acetophenones, benzophenones, Michler's benzoyl benzoate, α-amyloxim ester, thioxanthones, propiophenones, benzyls, benzoins, and acylphosphine oxides. Further, it is preferable to mix a photosensitizer to use, and specific example of the photosensitizer include n-butylamine, triethylamine, poly-n-butylphosphine, and the like.

As the photopolymerization initiator, in a case of resins having a radically polymerizable unsaturated group, acetophenones (for example, 1-hydroxy-cyclohexyl-phenyl-ketone marketed as trade name Irgacure 184 (manufactured by Ciba Specialty Chemicals Inc., Irgacure is a trademark)), benzophenones, thioxanthones, propiophenones, benzyls, acylphosphine oxides, benzoin, or benzoin methyl ether is preferably used singly, or used as a mixture thereof. Further, as the photopolymerization initiator, in a case of resins having a cationically polymerizable functional group, an aromatic diazonium salt, an aromatic sulfonium salt, an aromatic iodonium salt, a metallocene compound, or benzoin sulfonate is preferably used singly, or used as a mixture thereof. The addition amount of the photopolymerization initiator is preferably 0.1 to 10 parts by weight with respect to 100 parts by weight of the ionizing radiation-curable composition.

Examples of the solvent-drying resin, which is mixed in the ionizing radiation-curable resin to be used, include mainly thermoplastic resins.

As the above-mentioned thermoplastic resins, resins generally exemplified are used. By adding the solvent-drying resin, coat defects of a coated surface can be effectively prevented. Specific examples of preferable thermoplastic resins include styrenic resins, (meth)acrylic resins, vinyl acetate resins, vinyl ether resins, halogen-containing resins, alicyclic olefin resins, polycarbonate resins, polyester resins, polyamide resins, cellulose derivatives, silicone resins, and rubbers or elastomers.

As the thermoplastic resin, a resin, which is usually non-crystalline and soluble in organic solvents (particularly, a common solvent in which a plurality of polymers or curable compounds can be dissolved), is preferably used. Particularly, resins which are superior in molding properties or film-forming properties, transparency and weather resistance, for example, styrenic resins, (meth)acrylic resins, alicyclic olefin resins, polyester resins, and cellulose derivatives (cellulose esters, etc.) are preferable.

In accordance with a preferred aspect of the present invention, when a material of the light-transmitting substrate is a cellulose resin such as triacetyl cellulose "TAC", preferable specific examples of the thermoplastic resins include cellulose resins such as nitrocellulose, acetyl cellulose, cellulose acetate propionate, ethyl hydroxyethyl cellulose and the like. By use of cellulose resins, adhesion between the light-transmitting substrate and the hard coat layer, and transparency can be improved.

Examples of the thermosetting resin, which can be used as the resin having a curing reactivity, include a phenolic resin, a urea resin, a diallylphthalate resin, a melanin resin, a guanamine resin, an unsaturated polyester resin, a polyurethane resin, an epoxy resin, an aminoalkyd resin, a melamine-urea cocondensation resin, a silicon resin, a polysiloxane resin, and the like. When the thermosetting resin is used, it can also be used in combination with a curing agent such as a crosslinking agent or a polymerization initiator, a polymerization accelerator, a solvent, or a viscosity adjustment agent as required.

The composition for a hard coat layer may contain fine particles having ability to form projections and depressions. In this case, the hard coat layer to be formed comes to have a surface roughness and can be an antiglare layer having an antiglare property.

As the fine particles having ability to form projections and depressions, several types of fine particles which are different in types, sizes and shapes may be appropriately selected and used. Generally, plastic beads such as polystyrene beads, melamine beads, acrylic (polymethyl methacrylate, etc.) beads, acrylic-styrene beads, benzoguanamine-formaldehyde beads, polycarbonate beads, polyethylene beads and the like, having a diameter of 1 μm or more and 20 μm or less, or silica beads are used. Several types of beads can be simultaneously used, and for example, plastic beads such as acrylic beads having a particle diameter of 1 to 20 μm (preferably, 1 to 10 μm) may be used in combination with nonspherical silica beads having a particle diameter of 1 to 3 μm.

The composition for a hard coat layer can be obtained by mixing the curable resins and the above fine particles having ability to form projections and depressions in a proper solvent, for example, alcohols such as isopropyl alcohol, methanol and ethanol; ketones such as methyl ethyl ketone (MEK), methyl isobutyl ketone (MIBK) and cyclohexanone; esters such as methyl acetate, ethyl acetate and butyl acetate; halogenated hydrocarbons; aromatic hydrocarbons such as toluene and xylene; or mixtures thereof.

Further, the composition for a hard coat layer may contain a fluorine or silicone leveling agent. The composition for a hard coat layer containing the above leveling agent can improve the coating applicability and impart an effect of scratching resistance to the hard coat layer to be formed.

Examples of methods of applying the composition for a hard coat layer onto the light-transmitting substrate include coating methods such as a roller coating method, a Mayer bar (metering coating rod) coating method, a gravure coating method, and a die coating method.

After applying the composition for a hard coat layer, drying and ultraviolet-curing are performed as required.

Specific examples of an ultraviolet light source include light sources of an ultra high-pressure mercury lamp, a high-pressure mercury lamp, a low-pressure mercury lamp, a carbon arc lamp, a black light fluorescent lamp and a metal halide lamp.

As a wavelength of the ultraviolet light, a wavelength band of 190 to 380 nm can be used.

Specific examples of the electron beam source include various electron beam accelerators of a Cockcroft-Walton type, a van de Graaff type, a resonance transformer type, an insulating core transformer type, or a linear type, a Dynamitron type and a high-frequency type.

By curing the curable resin, the hard coat layer can be formed on the light-transmitting substrate. In a case of containing the fine particles having ability to form projections and depressions, the fine particles having ability to form projections and depressions in the curable resin are fixed to form a desired surface roughness at the outermost surface of the hard coat layer (that is, an antiglare layer is formed on the light-transmitting substrate).

The step of forming the optical layered body may have a step of forming a surface adjustment layer on the antiglare layer with a composition for a surface adjustment layer containing a resin binder when the hard coat layer is an antiglare layer having a surface roughness at its surface.

The surface adjustment layer is a layer for adjusting the surface roughness of the antiglare layer having projections and depressions to a more preferable shape. Particularly in the antiglare layer, there is a problem that a black color tone is poor (black color looks grayish because light is scattered at a projection and depression face), and by forming the surface adjustment layer, this problem can be improved. Herein, a property in which the black color tone is improved and a black color looks black with a gloss is referred to gloss blackness.

The composition for a surface adjustment layer contains a resin binder. The resin binder is not particularly limited, but a transparent resin binder is preferable and examples of the resin binder include ionizing radiation-curable resins which are resins to be cured with ultraviolet light or electron beams. Further, the composition for a surface adjustment layer preferably contains the solvent and the leveling agent described above.

As described above, the surface adjustment layer is effective for improving the gloss blackness. On the other hand, the gloss blackness is improved by the surface adjustment layer, but the antiglare property may be deteriorated in some cases.

Accordingly, for the purpose of improving the antiglare property without impairing the gloss blackness, the surface adjustment layer may contain a fluid adjuster. As the fluid adjuster, organic fine particles or inorganic fine particles are generally employed. As the fluid adjuster, preferably, colloidal silica, ATO, zirconia ultrafine particles, ultrafine antimony oxide particles or the like is used, and colloidal silica is particularly preferable. Its preferable size is about 1 to 70 nm. In addition, in the present invention, the "colloidal silica" means a colloid solution obtained by dispersing silica particles in colloidal state in water or an organic solvent. With respect to the particle size (diameter) of the colloidal silica, it is preferable that the particle is the ultrafine particle of 1 to 70 nm. Here, the particle size of the colloidal silica in the present invention refers to an average particle diameter measured by a BET method (the average particle diameter is calculated by measuring the surface area by a BET method and carrying out conversion into the diameter assuming the particles to be truly spherical).

Further, the surface adjustment layer may be a layer having a function of imparting antistatic property, adjustment of a refractive index, increase in hardness and an antifouling property in addition to the above-mentioned functions. In this case, the surface adjustment layer can be formed from the composition for a surface adjustment layer containing other additives (e.g., an antifouling agent) as required. Particularly in a case of containing the antifouling agent, since the degree of recovery from fouling of the surface of the optical layered body to be prepared is excellent and the anti-contamination property such as a property of preventing fingerprints from adhering is excellent, it is preferable.

A method for forming the surface adjustment layer is not particularly limited and the surface adjustment layer can be formed by applying the composition for a surface adjustment layer, which is obtained by mixing, for example, the above organic fine particles or inorganic fine particles, a binder resin (including resin components such as a monomer and an oligomer), a solvent, and an arbitrary component, onto the antiglare layer.

The composition for a surface adjustment layer can be applied by publicly known methods of application such as a Mayer bar (metering coating rod) coating method, a roller coating method, a gravure coating method, and a die coating method. After applying the composition for a surface adjustment layer, drying and curing are performed as required.

Further, examples of the method for forming the surface adjustment layer include the same methods as in the hard coat layer.

Further, the antiglare layer may be a single layer or a multilayer, but with respect to its surface roughness, if denoting a mean spacing of a projection and depression of the outermost layer of the optical layered body by Sm, a mean inclination angle of the projection and depression by θa, and ten-point average roughness of the projection and depression by Rz (definitions of Sm, θa and Rz are based on JIS B 0601 1994), it is preferable that Sm is 40 μm or more and 600 μm or less, θa is 0.3° or more and 5.0° or less, and Rz is 0.3 μm or more and 4.0 μm or less.

The step of forming the optical layered body may have a step of forming a low refractive index layer on the hard coat layer.

The low refractive index layer is a layer to play a role of decreasing a reflectance of light when external light (for example, fluorescent lamp, natural light, etc.) is reflected off the surface of the optical layered body. The low refractive index layer preferably has a refractive index of 1.45 or less, particularly preferably 1.42 or less, and most preferably 1.35 or less.

Further, a dried thickness of the low refractive index layer is not particularly limited, but it may be appropriately set within a range of about 30 nm to 1 μm in general.

The low refractive index layer is preferably composed of any one of 1) a resin containing silica or magnesium fluoride, 2) fluororesin being a low refractive index resin, 3) fluororesin containing silica or magnesium fluoride, and 4) a thin film of silica or magnesium fluoride. The same resins as those composing the composition for a hard coat layer can be used for resins other than the above-mentioned fluororesin.

As the above-mentioned fluororesin, a polymerizable compound containing fluorine atoms at least in a molecule or a polymer thereof can be used. The above-mentioned polymerizable compound is not particularly limited, but a polymerizable compound having a curing and reactive group such as an ionizing radiation-curable group or a heat-curable polar group is preferable. Further, compounds having these reactive groups simultaneously together may also be used. In contrast to this polymerizable compound, the above-mentioned polymer is a polymer not having the above reactive group at all.

In forming the low refractive index layer, the low refractive index layer can be formed by use of, for example, a composition (a composition for a refractive index layer) containing a raw material component. More specifically, a solution or a dispersion formed by dissolving or dispersing the raw material component (resin, etc.) and the additives (e.g., "particles having voids" described later, a polymerization initiator, an antistatic agent, an antiglare agent, an antifouling agent, etc.) added as required in a solvent is used as a composition for a low refractive index layer, and a coat obtainable from the above composition is formed, and the coat is cured, and whereby a low refractive index layer can be obtained. In addition, the additives such as the polymerization initiator, the antistatic agent, the antiglare agent, the antifouling agent, etc. are not particularly limited, and publicly known additives are used. Particularly in a case of containing the antifouling agent, since the degree of recovery from fouling of the surface of the optical layered body to be prepared is excellent and the anti-contamination property such as a property of preventing fingerprints from adhering is excellent, it is preferable.

In the low refractive index layer, "fine particles having voids" are preferably used as a low refractive index agent. The "fine particles having voids" can reduce the refractive index of the low refractive index layer while maintaining layer strength of the low refractive index layer. In the present invention, the term "fine particles having voids" means particles having a structure in which the inside of the particle is filled with vapor and/or a porous structure including vapor is formed, and a characteristic that the refractive index is decreased in inverse proportion to occupancy of the vapor in the particle compared with the particle inherent refractive index. Further, in the present invention, the particle in which a nano porous structure can be formed inside and/or in at least a part of the particle surface, based on the configuration, the structure and the flocculated state of the fine particles and the dispersed state of fine particles within a coat. The refractive index of the low refractive index layer using this fine particle can be adjusted to a refractive index of 1.30 to 1.45.

Examples of the inorganic fine particles having voids include silica fine particles prepared by a method disclosed in Japanese Kokai Publication 2001-233611. Further, silica particles prepared by production methods described in such as Japanese Kokai Publication Hei-7-133105, Japanese Kokai Publication 2002-79616, and Japanese Kokai Publication 2006-106714, may be used. Since the silica particle having voids is easily produced and has its own high hardness, their layer strength is improved and it becomes possible to adjust the refractive index to a refractive index of about 1.20 to 1.45 when the particles are mixed with the binder to form the low refractive index layer. Particularly, specific examples of organic fine particles having voids include a hollow polymer fine particle prepared by using a technology disclosed in Japanese Kokai Publication 2002-80503.

The above solvent is not particularly limited, and examples of the solvent include solvents exemplified in the description of the composition for a hard coat layer, and preferable solvents are methyl isobutyl ketone, cyclohexanone, isopropyl alcohol (IPA), n-butanol, t-butanol, diethyl ketone, PGME, and the like.

A method of preparing the composition for a low refractive index layer may be employed as long as each component can be mixed uniformly, and the composition may be prepared according to a publicly known method. For example, each component can be mixed by use of publicly known apparatus described in the description of the composition for a hard coat layer.

Further, as a method of forming a coat, publicly known methods may be employed. For example, various methods described in the description of the formation of the hard coat layer can be used.

A method of curing a coat obtained may be appropriately selected in accordance with the content of the composition. For example, if the composition is ultraviolet-curable, the coat obtained from the composition may be cured by radiating ultraviolet light to the coat. When a heating means is used for curing treatment, a heat polymerization initiator which generates for example radicals by heating to initiate the polymerization of a polymerizable compound is preferably added.

Furthermore, the step of forming the optical layered body may include a step of forming the antifouling layer or the antistatic layer. A method for forming the antifouling layer or the antistatic layer is not particularly limited and methods similar to publicly known methods can be employed.

(Inspection Step)

An optical film exemplified in the optical layered body thus obtained is subjected to the following inspection step. That is, after the surface of the optical film is artificially fouled, light is radiated to the optical film and scattered light reflected off or passing through the optical film is detected to evaluate a degree of fouling of the optical film. This evaluation may be performed automatically in a production line of the optical film, or may be performed separately on the optical films (test sample) sampled from the production line at prescribed intervals immediately after the production of the optical film. Such details of the evaluation method that it is preferable to evaluate the surface of the optical film based on a L*a*b* color model specified by International Commission on Illumination (CIE) are not given here because it is possible to utilize the principle, technique, equipment and the like described in paragraphs of the evaluation method of fouling and the fouling evaluation apparatus. In addition, in the above-mentioned inspection step, the optical film is not artificially fouled and the surface condition immediately after obtaining the optical film may be evaluated. By performing such an evaluation, the surface condition (degree of fouling) of the obtained optical film can be evaluated, and therefore the occurrence of a failure due to impurities or fouling can be easily detected even when impurities or fouling is contaminated in a production line.

In the above-mentioned inspection step, an evaluation of the surface condition of the optical film is the evaluation of the degree of fouling carried out after being artificially fouled. Accordingly, quality of antifouling property of the optical film can be evaluated. Particularly when the optical films are sampled from the production line at prescribed intervals immediately after the production thereof and these sampled optical films (test sample) are separately evaluated, the above-mentioned evaluation is preferably performed. Such details of the evaluation method that the above artificial fouling is preferably fouling due to fingerprint-adhering are not given here because it is possible to utilize the principle, technique, equipment and the like described in paragraphs of the evaluation method of fouling and the fouling evaluation apparatus.

In the inspection step, the degree of recovery from fouling of the surface of the optical film may be evaluated by cleaning the surface of the optical film and evaluating the degree of fouling of the optical film again after evaluating the degree of fouling of the surface of the optical film. By such a further applicable evaluation, quality of recovery performance of cleanliness of the optical film can be evaluated. Particularly when the optical films are sampled from the production line at prescribed intervals immediately after the production thereof and these sampled optical films (test sample) are separately evaluated, the above-mentioned further applicable evaluation is preferably performed. Details of the evaluation method are not given here because it is possible to utilize the principle, technique, equipment and the like described in paragraphs of the evaluation method of fouling and the fouling evaluation apparatus.

In addition, the inspection step described above can be performed after the completion of the step of obtaining the optical members as described above, but it can also be performed at an appropriate stage (even in a semi-product during a production step, if the necessity or significance to evaluate the fouling arises) during the step of obtaining the optical members. Further, when the inspection step is performed after the completion of the step of obtaining the optical members, a time interval between two steps is arbitrary (such as 1 second, 1 day and 1 month) and it may be appropriately set.

[Optical Layered Body]

In the optical layered body of the present invention, a difference between $\Delta E^*ab$ specified by International Commission on Illumination (CIE) after the surface is artificially fouled and $\Delta E^*ab$ specified by International Commission on Illumination (CIE) after the surface is subjected to a cleaning treatment (degree of recovery from fouling) is 1.5 or less.

When the above-mentioned degree of recovery from fouling is more than 1.5, even if fouling can be removed from a fouled part by a cleaning treatment, a color difference between the part subjected to a cleaning treatment and a part not fouled becomes large and a practical display product cannot be obtained. The degree of recovery from fouling is preferably 1.3 or less, and more preferably 1.0 or less.

Herein, the description of "the degree of recovery from fouling" is not given here because it is possible to utilize the evaluation method of fouling of the present invention described above and the principle, technique, equipment and the like described in a paragraph of the inspection step of the production method of the optical member of the present invention.

The optical layered body, in which the anti-contamination property (property of preventing fingerprints from adhering) represented by $\Delta E^*ab$ specified by International Commission on Illumination (CIE) after the surface is artificially fouled is 3.5 or less, also constitutes the present invention.

In a case where the anti-contamination property is more than 3.5, when viewing displayed substances such as characters through the optical layered body of the present invention, the displayed substances look distorted and a practical display cannot be obtained. The anti-contamination property is preferably 2.5 or less, more preferably 1.5 or less, and most preferably 1.0 or less.

Herein, the description of "the anti-contamination property" is not given here because it is possible to utilize the evaluation method of fouling of the present invention described above and the principle, technique, equipment and the like described in a paragraph of the inspection step of the production method of the optical member of the present invention.

Examples of the optical layered body of the present invention having such a degree of recovery from fouling and an anti-contamination property (property of preventing fingerprints from adhering) include optical layered bodies having excellent antireflection performance described above and a constitution in which at least a hard coat layer is formed on a light-transmitting substrate. Further, for example, an antireflection layered body (Anti Reflection product), which has a layer constitution of a light-transmitting substrate/a hard coat layer (it may also serve as a high refractive index layer)/a high refractive index layer (or a medium refractive index layer)/a low refractive index layer, a light-transmitting substrate/a hard coat layer (it may also serve as a high refractive index layer)/a low refractive index layer or the like and is superior in antireflection performance, an antiglare optical layered body (Anti Glare product), which has a surface roughness at the outermost surface and a layer constitution of a light-transmitting substrate/an antiglare layer (having a hard coat function) and the like can be included. In addition, the antiglare layer may be a monolayer or a multilayer. Further, the low refractive index layer may be formed on the antiglare layer. Furthermore, each layer of the antireflection layered body and the antiglare optical layered body may have various functions such as an antistatic property and the like, or the antireflection layered body and the antiglare optical layered body may have these functions between layers of these layered bodies.

Herein, the optical layered body of the present invention comes to have different surfaces between the case of being an antireflection layered body (Anti Reflection product) and the case of being an antiglare optical layered body (Anti Glare product). However, even when the optical layered body has any of these constitutions, the optical layered body of the present invention has the degree of recovery from fouling and the anti-contamination property (property of preventing fingerprints from adhering) described above.

Furthermore, the optical layered body of the present invention may achieve the degree of recovery from fouling and the anti-contamination property (property of preventing fingerprints from adhering) described above simultaneously.

The optical layered body of the present invention can be provided in publicly known display products such as cathode ray tube (CRT) display devices, liquid crystal displays (LCD), plasma displays (PDP), electroluminescence displays (ELD) and the like.

Such a display product including the optical layered body of the present invention also constitutes the present invention.

Since the display product of the present invention includes the above-mentioned optical layered body of the present invention, it has an excellent anti-contamination property of a surface and has an excellent property of recovering from fouling even when it is fouled.

Examples

Next, the present invention will be described in more detail by way of examples, but the present invention is not limited to these examples as long as the present invention is not departing from the gist thereof.

(Preparation of Optical Layered Body and Test Sample)

First, a composition having a solid content of 40.5% by weight was prepared by adequately mixing the following materials. This composition was filtrated with a polypropylene filter having a pore size of 30 μm to prepare a composition for an antiglare layer.
Ultra Violet Curable Resin;
  Pentaerythritol triacrylate (PETA) (refractive index 1.51) 2.20 parts by weight
  Isocyanuric acid modified diacrylate M-215 (manufactured by Nippon Kayaku Co., Ltd., refractive index 1.51) 1.21 parts by weight
  Polymethyl methacrylate (Molecular weight 75000) 0.34 parts by weight
Photocuring Initiator;
  Irgacure 184 (manufactured by Ciba Specialty Chemicals Inc.) 0.22 parts by weight
  Irgacure 907 (manufactured by Ciba Specialty Chemicals Inc.) 0.04 parts by weight
First Light-Transmitting Fine Particle;
  Monodisperse acrylic bead (particle diameter 9.5 μm, refractive index 1.535) 0.68 parts by weight
Second Light-Transmitting Fine Particle;
  Nonspherical silica ink (average particle diameter 1.5 μm, solid content 60%, silica component is 15% of a total solid content) 0.64 parts by weight
Leveling Agent;
  Silicone leveling agent 0.02 parts by weight
Solvent;
  Toluene 5.88 parts by weight
  Cyclohexanone 1.55 parts by weight Next, a composition was prepared by adequately mixing the following materials. This composition was filtrated with a polypropylene filter having a pore size of 10 μm to prepare a composition for a surface adjustment layer having a solid content of 40.5% by weight.
  Polyfunctional urethane acrylate UV-1700B (manufactured by Nippon Synthetic Chemical Industry Co., Ltd., refractive index 1.51) 31.1 parts by weight
  Aronix M-315 (trade name, triacrylate of 3-mole ethylene oxide adduct of isocyanuric acid manufactured by Toagosei Co., Ltd.) 10.4 parts by weight
Photocuring Initiator;
  Irgacure 184 (manufactured by Ciba Specialty Chemicals Inc.) 1.49 parts by weight
  Irgacure 907 (manufactured by Ciba Specialty Chemicals Inc.) 0.41 parts by weight
Antifouling Agent;
  UT-3971 (manufactured by Nippon Synthetic Chemical Industry Co., Ltd.) (addition by 5% of solid matter) 2.07 parts by weight
Solvent;
  Toluene 525.18 parts by weight
  Cyclohexanone 60.28 parts by weight Using a biaxial stretching polyethylene terephthalate film (manufactured by TOYOBO Co., Ltd., trade name "A4300") having a thickness of 100 μm as a transparent substrate, a composition for an antiglare layer was applied onto the film with a wire wound rod for coating (Mayer bar (metering coating rod)) #8, and the applied composition was heated to dry for 1 minute in an oven of 70° C. to evaporate the solvent fraction, and then a coat was cured by irradiating ultraviolet light to the coat in such a way that an exposure becomes 30 mJ to form an antiglare layer. With respect to a surface roughness of the formed antiglare layer, Sm was 78 μm, Rz was 3.354 μm, and θa was 4.8°.

Furthermore, a composition for a surface adjustment layer was applied onto the antiglare layer with a wire wound rod for coating (Mayer bar (metering coating rod)) #10, and the applied composition was heated to dry for 1 minute in an oven of 70° C. to evaporate the solvent fraction, and then a coat was cured by irradiating ultraviolet light to the coat in such a way that an exposure becomes 100 mJ under nitrogen purge (oxygen content 200 ppm or less) to form a surface adjustment layer to obtain an optical layered body (The total thickness of the antiglare layer on the substrate: about 12.5 μm). With respect to a projection and recess shape of this antiglare optical layered body, Sm was 145 μm, Rz was 0.51 μm, and θa was 0.38°.

A film of 10 cm×10 cm was cut off from the film-like optical layered body thus obtained as test samples for evaluation of fouling. Number of the test samples was 3.

Example 1

Fouling (Adhesion of Fingerprints) of Test Sample

A pseudo fingerprint liquid (artificial fingerprint liquid) containing triolein and fine particles was pressed against the test sample by an indenter (a contact surface is a circle of 12 mm in diameter, this diameter was premised on the human's fingers) to which a load of 500 g was applied to allow the artificial fingerprint liquid to adhere to the surface of the test sample. It was possible to allow the fingerprint to adhere quantitatively to the test sample by this adhesion method, and in this experiment, 0.04 mg of the artificial fingerprint per 1 mm$^2$ was adhered under the above-mentioned adhesion conditions.

(Test for Evaluation of Fouling)

The test sample (reference) before a fingerprint-adhering treatment and the test sample subjected to a fingerprint-adhering treatment were bonded to a black acrylic plate with a pressure-sensitive adhesive sheet by a roller, respectively, without producing wrinkles or sagging in a film, using an acrylic pressure sensitive adhesive (manufactured by Hitachi Chemical Co., Ltd., DA-1000) for an optical film. Then, the spectral diffuse reflectance of each evaluation sample was measure with a spectrophotometer V-650 (manufactured by JASCO Corporation, range of measuring wavelength 190 nm to 900 nm) equipped with a 150 mm$\phi$ integrating sphere unit manufactured by JASCO Corporation. Specifically, chromaticity x, y values and luminance Y values of diffuse reflected light were determined, these data was converted to $a*b*L*$ values, and a color difference ($\Delta E*ab$) between the reference test sample and the test sample subjected to fingerprint-adhering was determined to digitize and quantify the degree of fingerprint-adhering. In addition, it is said that the test sample having smaller color difference has a higher property of preventing fouling substances (fingerprints in this case) from adhering. The definitions of x, y, Y values, an $a*b*L*$ value and a color difference $\Delta E*ab$ of the present invention were based on provisions of according to International Commission on Illumination (CIE).

The operation, in which the spectral diffuse reflectance of the test sample subjected to a fingerprint-adhering treatment prepared by the above-mentioned method was measured by the spectrophotometer described above to determine chromaticity x, y values and luminance Y values of diffuse reflected light, and these data was converted to $a*b*L*$ values, and a color difference ($\Delta E*ab$) between the reference test sample and the test sample were determined, was repeated 3 times in total. In addition, when the spectral diffuse reflectance was measured, the test sample was positioned by a jig in such away that a measuring spot (measuring range is a circle of 0.8 mm$\phi$) was positioned in a circle of the indenter described above to secure accuracy. As the result of three measurement of the color difference, $\Delta E*ab=3.36\pm0.03$. From this result, it was found that the fouling (fingerprint-adhering) of the test sample can be quantitatively evaluated without variations and with high reproducibility. In addition, the result of three actual measurement of $\Delta E*ab$ are as follows.

(Result of $\Delta E*ab$)
 1st measurement 3.33
 2nd measurement 3.39
 3rd measurement 3.36

Next, after the fouling substance (artificial fingerprint liquid) adhering to each test sample was cleaned by the following method, the degree of fouling of each test sample was evaluated again, and thereby the degree of recovery from fouling of each test sample was evaluated.

(Cleaning Treatment of Fouling Substance)

A wiping item (Kim-Wipe (trademark)) was wrapped around an indenter portion of an abrasion resistance tester TYPE F manufactured by HEIDON, Shinto Scientific Co., Ltd. and the indenter portion was pressed against a sample in which adhesion was evaluated, and moved to and fro twenty times in a width of 10 cm under a load of 500 g to wipe out fouling substances, and the test sample was subjected to a cleaning treatment.

(Evaluation of Degree of Recovery from Fouling of Each Test Sample)

After the above cleaning, in the same manner as in Test for evaluation of fouling described above, the spectral diffuse reflectance and the color difference of the test samples subjected to a cleaning treatment prepared in the same manner were measured three times in total with a spectrophotometer. As a result of this, it was found that the color differences at the surface of the test samples subjected to a cleaning treatment all fall within a rage of $\Delta E*ab=0.66\pm0.05$ and the degree of recovery by cleaning can be quantitatively evaluated with high reproducibility. The result of three actual measurement of $\Delta E*ab$ are as follows.

(Result of $\Delta E*ab$)
 1st measurement 0.71
 2nd measurement 0.61
 3rd measurement 0.66

Furthermore, the present inventors noted $\Delta E*ab$, and {value before cleaning (average)−value after cleaning (average)} was taken as a numerator and a value before cleaning (average) was taken as a denominator and the resulting fraction is multiplied by 100 to determine a recovery factor of cleanliness by cleaning, and consequently it was found that the recovery factor was 80.36%. In addition, generally, when variations in numerals of evaluation results are large, a median is employed in order to minify an effect of extremely large or small value on a statistic, but in the evaluation method of the present invention, since variations in numerals is small, a significant recovery factor of cleanliness can be obtained by using an average value.

Comparative Example 1

(1) Visual Evaluation of Degree of Fouling (After Fouling Treatment)

Three test samples produced by the above-mentioned method were prepared, and these test samples were artificially fouled in the same manner as in "Fouling (adhesion of fingerprints) of test sample" of Example 1. The degrees of fouling of these test samples were visually (by eyes) evaluated compared with the evaluation measure sample previously prepared.

The evaluation by eyes was carried out as follows. First, evaluation measure samples corresponding to five levels of the extent of fingerprint-adhering (fouling) were previously prepared. In addition, antiglare layers described Examples were prepared as an optical layered body to be a base of the evaluation measure sample, and five levels of fouling substances were adhered to the surfaces of the antiglare layers as described below to prepare the evaluation measure samples. Then, this evaluation measure sample and the above test sample subjected to a fouling treatment were lined up and these samples were visually observed under illuminance of 1000 lux. In the evaluation, the test sample was rated based on the five levels of evaluation measure samples. The level of evaluation measure sample, whose fouling level is most close to that of the test sample, is taken as an evaluated value. Here, a case where fouling is most heavy is rated as "level 1" and a case where the cleanliness is equal to that of a surface to which fingerprints do not adhere (in a case of no adhesion of fingerprints) is rated as "level 5". Further, the evaluation was carried out by different five observers. The obtained results are shown in Table 1.

(Production Method of Evaluation Measure Sample of Levels 1 to 5)

By the same method as in "Fouling (adhesion of fingerprints) of test sample" of Example 1, an artificial fingerprint liquid was pressed against an antifouling layer by an indenter to which a load of 500 g is applied to allow the fingerprint fouling to adhere to the antiglare layer in an amount 0.04 mg per 1 m². However, the concentration of the used pseudo fingerprint liquid was altered as follows to prepare 5 levels of evaluation measure sample.

Level 1 A pseudo fingerprint liquid having a concentration which is four times that of level 4

Level 2 A pseudo fingerprint liquid having a concentration which is three times that of level 4

Level 3 A pseudo fingerprint liquid having a concentration which is two times that of level 4

Level 4 A pseudo fingerprint liquid having a basic concentration

Level 5 A pseudo fingerprint liquid did not adhere (2) Visual Evaluation of Degree of Recovery from Fouling (After Cleaning Treatment)

Next, the above-mentioned three test samples were subjected to a cleaning treatment in the same manner as in a paragraph of "Cleaning treatment of fouling substance" of Example 1. Then, after cleaning, a degree of recovery from fouling of the test samples was evaluated in the same manner as in the visual observation based on five levels of evaluation measure samples in the above (1). The obtained results are shown in Table 1.

TABLE 1

| Observer | After fouling treatment | After cleaning treatment |
|---|---|---|
| Test sample 1 | | |
| A | Level 1 | Level 4 |
| B | Level 1 | Level 4 |
| C | Level 1 | Level 3 |
| D | Level 1 | Level 5 |
| E | Level 1 | Level 4 |
| Test sample 2 | | |
| A | Level 1 | Level 3 |
| B | Level 1 | Level 4 |
| C | Level 1 | Level 3 |
| D | Level 1 | Level 5 |
| E | Level 1 | Level 5 |
| Test sample 3 | | |
| A | Level 1 | Level 4 |
| B | Level 1 | Level 3 |
| C | Level 1 | Level 3 |
| D | Level 1 | Level 4 |
| E | Level 1 | Level 4 |

From these results, it is found that even if the level of illuminance is the same, a feeling of the degree of fouling varies from a person to a person and the test samples show large variations in the fouling evaluation level particularly after the cleaning treatment. It is said that the evaluation depending on only human's eyes has a problem in reliability and reproducibility as an evaluation method. Particularly displays are marketed products in which the evaluation by human's eyes is important but only sensory evaluation cannot attain reproducibility.

On the other hand, by quantifying fouling and properties recovering from fouling and combining this value with sensory evaluation, production efficiency can be improved by a large amount.

Example 2

Four types of AR test samples (4 to 7) with a flat surface, which does not have a surface roughness, were prepared using the following compositions and method. Herein, the evaluations of how much ΔE*ab in a degree of recovery from fouling, which is preferable for a display surface, corresponds was carried out. A level of the antifouling property of the test samples (4 to 7) themselves was altered in four levels in order to compare the degree of recovery from fouling. In order to evaluate severely, AR layered bodies with a flat surface, which does not have a surface having a surface roughness, were used as each test sample (the reason for this is that a surface having a surface roughness becomes difficult in judging a degree of fouling because external light is reflected off this surface.) Number of repeats n was set at 3.

(Production of Test Sample 4)
Composition for a Hard Coat Layer
Urethane acrylate (UV-1700B; manufactured by Nippon Synthetic Chemical Industry Co., Ltd.) 5 parts by weight
Polyester acrylate (M-9050; manufactured by Toagosei Co., Ltd.) 5 parts by weight
Polymerization initiator (Irgacure 184; manufactured by Ciba Specialty Chemicals Inc.) 0.4 parts by weight
Methyl ethyl ketone 10 parts by weight
Compositions for a Low Refractive Index Layer
Solution containing treated silica sol (silica sol solid content 20% by weight, "fine particle having voids, solution; methyl isobutyl ketone") 14.3 parts by weight
Pentaerythritol triacrylate (PETA) 1.95 parts by weight
Polymerization initiator (Irgacure 127; manufactured by Ciba Specialty Chemicals Inc.) 0.1 parts by weight
Antifouling agent (fluorine base; MEGAFAC RS: manufactured by DIC Corporation, solid matter) 0.07 parts by weight
Methyl isobutyl ketone 54.0 parts by weight
Propylene glycol monomethyl ether acetate 29.5 parts by weight An amount of the antifouling agent in this composition is 1.5% with respect to the solid matter.

Production Method
A triacetyl cellulose (TAC) film (manufactured by FUJIFILM Corporation, TF 80UL, thickness 80 μm) was prepared, and the composition for a hard coat layer was applied (bar coating) onto the surface of the film in a wet weight of 20 g/m² (dried weight of 10 g/m²), and then the applied composition on the film was dried at 50° C. to eliminate a solvent. Thereafter, the dried composition was cured by irradiating ultraviolet light to the composition at an exposure dose of 50 mJ/cm² with an ultraviolet irradiation apparatus (manufactured by Fusion UV Systems Japan K.K.) to form a hard coat layer of 10 μm in thickness.

Next, the composition for a low refractive index layer was applied (bar coating) onto the surface of the hard coat layer in a dried weight of 0.1 g/m², and then the applied composition was dried at 40° C. to eliminate a solvent. Thereafter, ultraviolet light was radiated to the composition at an exposure dose of 200 mJ/cm² with the ultraviolet irradiation apparatus (manufactured by Fusion UV Systems Japan K.K.) to produce an optical layered body (test sample 4). The low refractive index layer was formed so as to have such a film thickness that a reflectance becomes a local minimal value in the vicinity of a wavelength of 550 nm (a film thickness is 0.10 μm).

(Production of Test Sample 5)
A test sample 5 was prepared in the same manner as in the test sample 4 except for changing an amount of the antifouling agent in the composition for a low refractive index layer to 1.0% with respect to the solid matter.

(Production of Test Sample 6)
A test sample 6 was prepared in the same manner as in the test sample 4 except for changing an amount of the antifouling agent in the composition for a low refractive index layer to 0.3% with respect to the solid matter.

(Production of Test Sample 7)

A test sample 7 was prepared in the same manner as in the test sample 4 except for not adding the antifouling agent in the composition for a low refractive index layer.

(Evaluation of Degree of Recovery from Fouling)

Determination of Degree of Recovery from Fouling by ΔE*ab

It was evaluated which level a substance once fouled is recovered to by the same cleaning method.

Adhesion of a pseudo fingerprint liquid to the test samples 4 to 7 was carried out in the same manner as in a paragraph of "Fouling (adhesion of fingerprints) of test sample" of Example 1, and a spectral diffuse reflectance was measured in the same manner as in a paragraph of "Test for evaluation of fouling" of Example 1. Next, a cleaning treatment of a fouling substance was carried out in the same manner as in a paragraph of "Cleaning treatment of fouling substance" of Example 1 and the spectral diffuse reflectance of the cleaned test sample was measured to determine a color difference ΔE*ab between the cleaned layered body and the above layered body of fingerprint-adhering. Measurement was carried out in the same manner as in Example 1 to secure measuring accuracy. Three sheets of the test samples were measured similarly. The obtained results are shown in Table 2.

Evaluation of Practicality After Cleaning

The test samples 4 to 7 after cleaning the fouling substance were placed on a horizontal table under illuminance of 1000 lux and the test samples were visually observed from 30 cm above the test sample and a direction of 45 degrees from the test sample and a level of remaining fouling was rated according to the following criteria. In addition, since the test samples have an antireflection film, if the test samples were observed in a state of being stuck to a blackboard, a part where fouling remains exhibits a different interference color from that of a part not fouled and judgment can be easily made.

(Evaluation Criteria)

Good: A fouling substance is wiped out and at the same time, a difference in colors between the cleaned test sample and a test sample not fouled is small (practical).

Poor: A fouling substance is wiped out but a color of the cleaned test sample differs distinctly from that of a test sample not fouled (impractical).

TABLE 2

|  | ΔE * ab | | | |
| --- | --- | --- | --- | --- |
|  | 1st | 2nd | 3rd | Practicality |
| Test sample 4 | 1.07 | 1.03 | 1.12 | Good |
| Test sample 5 | 1.19 | 1.25 | 1.26 | Good |
| Test sample 6 | 1.82 | 1.76 | 1.74 | Poor |
| Test sample 7 | 2.67 | 2.70 | 2.69 | Poor |

(Preparation of Optical Layered Body and Test Sample, Having a Surface Roughness at Surface)

First, a composition having a solid content of 40.5% by weight was prepared by adequately mixing the following materials. This composition was filtrated with a polypropylene filter having a pore size of 30 μm to prepare a composition for an antiglare layer.

(Components of the Composition for an Antiglare Layer)
Ultra Violet Curable Resin
  Pentaerythritol triacrylate (PETA) (refractive index 1.51) 100 parts by weight
  Cellulose acetate propionate (molecular weight 50000) 1.25 parts by weight
Photocuring Initiator;
  Irgacure 184 (manufactured by Ciba Specialty Chemicals Inc.) 5 parts by weight
  Irgacure 907 (manufactured by Ciba Specialty Chemicals Inc.) 1 part by weight
Light-Transmitting Fine Particle;
  Monodisperse acrylic-styrene bead (particle diameter 3.5 μm, refractive index 1.54) 8.1 parts by weight
  Fluorine MEGAFAC RS (manufactured by DIC Corporation)
  1.73 parts by weight (1.5% of solid matter)
Solvent;
  Toluene 134 parts by weight
  Methyl isobutyl ketone 34 parts by weight (Production of Test Sample 8)

A triacetyl cellulose (TAC) film (manufactured by FUJIFILM Corporation, TF 80UL, thickness 80 μm) was prepared, and the composition for an antiglare layer was applied (bar coating) onto the surface of the film in a dried weight of 8 g/m$^2$, and then the applied composition on the film was dried at 70° C. to eliminate a solvent. Thereafter, the dried composition was cured by irradiating ultraviolet light to the composition at an exposure dose of 100 mJ/cm$^2$ with an ultraviolet irradiation apparatus (manufactured by Fusion UV Systems Japan K.K.) to form an antiglare layered body (test sample 8). With respect to a surface roughness of this layered body, Sm was 108 μm, Rz was 0.61 μm, and θa was 0.51°.

Each of test samples 9, 10 having a surface roughness at its surface were obtained in the same manner as in the test sample 8 except for changing an addition amount of the antifouling agent in the composition to the following amount.

Test sample 9: An addition amount of the antifouling agent was 1.0% of the solid matter.

Test sample 10: An addition amount of the antifouling agent was 0.3% of the solid matter.

On the obtained test samples 8 to 10, as with the test samples 4 to 7, the evaluations of how much ΔE*ab in a degree of recovery from fouling, which is preferable for a display surface, corresponds was carried out. The results of evaluations are shown in Table 3. Here, a level of the antifouling property of the test samples 8 to 10 themselves was altered in three levels in order to compare the degree of recovery from fouling.

TABLE 3

|  | ΔE * ab | | | |
| --- | --- | --- | --- | --- |
|  | 1st | 2nd | 3rd | Practicality |
| Test sample 8 | 0.55 | 0.59 | 0.52 | Good |
| Test sample 9 | 1.10 | 1.05 | 1.08 | Good |
| Test sample 10 | 1.62 | 1.66 | 1.62 | Poor |

An antiglare layer, in which the leveling agent in the composition for an antiglare layer prepared in Example 1 was changed to a fluorine antifouling agent (MEGAFAC RS, manufactured by DIC Corporation) and a surface adjustment layer was not formed, and an antiglare layer test sample, in which nonspherical silica having several kinds of average particle sizes, melamine beads having a particle diameter of 2 to 5 μm and polystyrene beads were used as the fine particle, were produced as other test samples having a surface roughness like the test samples 8 to 10, and the same tests as in the test samples 8 to 10 were tried, and consequently it has been shown that if ΔE*ab is 1.5 to 1.3 or less, the test sample has highly practical degree of recovery from fouling.

By using the evaluation method of the degree of recovery from fouling of the present invention, it is possible to simply make sure whether articles requiring the recovery from fouling (fingerprints adhere and are easily removed) such as an outermost surface of a display have a preferable level or not. In accordance with the present invention, it can be said that the surface has a recovering property if ΔE*ab is 1.5 or less. In addition, ΔE*ab is preferably 1.5 or less, more preferably 1.3 or less, and most preferably 1.0 or less for the surface for a display.

Example 3

Five types of AR test samples (11 to 15) with a flat surface were prepared in the same manner as in the test samples 4 to 7 of Example 2 except for using a fluorine antifouling agent "OPTOOL DAC (manufactured by DAIKIN INDUSTRIES, Ltd.)" as an antifouling agent. Herein, measurement of how much an anti-contamination property (property of preventing fingerprints from adhering, evaluated by ΔE*ab) is preferable for a surface for a display was carried out. The addition amounts of the antifouling agents are as follows.

Test sample 11: An addition amount of the antifouling agent was 1.3% with respect to the solid matter.
Test sample 12: An addition amount of the antifouling agent was 0.7% with respect to the solid matter.
Test sample 13: An addition amount of the antifouling agent was 0.3% with respect to the solid matter.
Test sample 14: The antifouling agent was not added.
Test sample 15: The optical layered body was prepared in the same manner as in the test sample 11 except that an antifouling agent was not added to the composition for a low refractive index layer and Novec EGC-1720 (manufactured by 3M, solid content 0.1%, diluted with hydrofluoroether) was applied onto the low refractive index layer in a film thickness of about 10 nm and a solvent is evaporated and the applied coat was cured at 110° C. for 1 minute to form an antifouling layer. In addition, a thickness of the antifouling layer was determined by observing the layer before and after applying a coat with a white interference precision microscope (ZygoNewView 6000 series manufactured by Zygo K.K.).

(Evaluation of Anti-Contamination Property)
Determination of Property of Preventing Fingerprints from Adhering by ΔE*ab Adhesion of a pseudo fingerprint liquid to the test samples 11 to 15 was carried out in the same manner as in a paragraph of "Fouling (adhesion of fingerprints) of test sample" of Example 1, and spectral diffuse reflectances of a reference test sample and the test samples with the fingerprint liquid were measured in the same manner as in a paragraph of "Test for evaluation of fouling" of Example 1 to determine color differences ΔE*ab. Measurement was carried out in the same manner as in Example 1 to secure measuring accuracy. Three sheets of the test samples were measured similarly. The obtained results are shown in Table 4.
Evaluation of Practicality by Fouling Next, the test samples 11 to 15 were bonded to a display monitor with 1280 pixel×1024 pixel using an acrylic pressure sensitive adhesive for an optical film, and a MS Mincho character "A" of 12 point in size was displayed beneath adhering fingerprints and read out visually from about 30 cm distance from the display. Ease of readout by a degree of fouling was judged under illuminance of 1000 lux according to the following criteria.

(Evaluation Criteria)
Good: A character looks with almost no distortion at a level at which the test sample can be used as a product.
Poor: A character looks distorted at a level at which the test sample cannot be used as a product.

TABLE 4

|  | ΔE * ab | | | |
|---|---|---|---|---|
|  | 1st | 2nd | 3rd | Practicality |
| Test sample 11 | 1.35 | 1.33 | 1.31 | Good |
| Test sample 12 | 2.81 | 2.79 | 2.84 | Good |
| Test sample 13 | 3.22 | 3.24 | 3.20 | Good |
| Test sample 14 | 4.31 | 4.29 | 4.33 | Poor |
| Test sample 15 | 0.89 | 0.92 | 0.90 | Good |

(Preparation of Optical Layered Body and Test Sample, Having a Surface Roughness at Surface)

Three types of layered bodies having a surface roughness at their surfaces were prepared in the same manner as in the test samples 8 to 10 of Example 2 except for changing an antifouling agent to a fluorine antifouling agent "OPTOOL DAC" (manufactured by DAIKIN INDUSTRIES, Ltd.) and changing an addition amount of the fluorine antifouling agent to the following amounts. Thereafter, test samples 16 to 18 were obtained in the same manner as in Example 1.

On the obtained test samples 16 to 18, as with the test samples 11 to 15, the evaluations of how much ΔE*ab in the anti-contamination property (property of preventing fingerprints from adhering), which is preferable for a display surface, corresponds was carried out. The results of evaluations are shown in Table 5. Here, a level of the antifouling property of the test samples 16 to 18 themselves was altered in three levels in order to compare the property of preventing fingerprints from adhering.

Test sample 16: An addition amount of the antifouling agent was 1.3% of the solid matter.
Test sample 17: An addition amount of the antifouling agent was 0.7% of the solid matter.
Test sample 18: An addition amount of the antifouling agent was 0.1% of the solid matter.

TABLE 5

|  | ΔE * ab | | | |
|---|---|---|---|---|
|  | 1st | 2nd | 3rd | Practicality |
| Test sample 16 | 1.05 | 1.08 | 1.10 | Good |
| Test sample 17 | 2.16 | 2.12 | 2.12 | Good |
| Test sample 18 | 3.87 | 3.83 | 3.84 | Poor |

Further, an antiglare layer, in which the leveling agent in the composition for an antiglare layer prepared in Example 1 was changed to a fluorine antifouling agent (OPTOOL DAC, manufactured by DAIKIN INDUSTRIES, Ltd.) and a surface adjustment layer was not formed, and an antiglare layer test sample, in which nonspherical silica having several kinds of average particle sizes, melamine beads having a particle diameter of 2 to 5 μm and polystyrene beads were used as the fine particle, were produced as other test samples having a surface roughness like the test samples 16 to 18, and the same tests as in the test samples 16 to 18 were tried, and consequently it has been shown that if ΔE*ab is about 3.5 or less, the test sample has highly practical anti-contamination property (property of preventing fingerprints from adhering).

By using the evaluation method of the prevention of fingerprint-adhering of the present invention, it is possible to simply make sure whether articles requiring the anti-contamination property (property of preventing fingerprints from adhering) such as an outermost surface of a display have a preferable anti-contamination property or not. In accordance with the present invention, it can be said that the surface has the anti-contamination property (property of preventing fingerprints from adhering) if $\Delta E^*ab$ is 3.5 or less. Furthermore, it can be said that the surface has the more excellent anti-contamination property (property of preventing fingerprints from adhering) if $\Delta E^*ab$ is 2.5 or less. $\Delta E^*ab$ is preferably 3.5 or less, more preferably 1.5 or less, and most preferably 1.0 or less for the surface for a display.

INDUSTRIAL APPLICABILITY

The evaluation method of fouling, the fouling evaluation apparatus, the production method and the optical layered body, which has the anti-contamination property (property of preventing fingerprints from adhering) and the degree of recovery from fouling, of the present invention can be preferably used in the fields of optical films such as an antireflection film for a display, an antireflection film for a touch panel and the like, and optical discs such as a CD, a DVD and the like.

The invention claimed is:

1. An evaluation method of fouling,
   wherein light is radiated to a test sample and
   scattered light reflected off or passing through the test sample is detected to evaluate a degree of fouling of the surface of the test sample; wherein the test sample is an optical layered body; wherein the surface of the test sample is artificially fouled due to fingerprint-adhering and wherein the evaluation method is carried out using a fouling evaluation apparatus that
   comprises a setting table of a test sample,
   a light source for radiating light to the test sample provided on the setting table,
   an integrating sphere for collecting scattered light reflected off or passing through the test sample, and
   a scattered light detector for detecting collected scattered light to evaluate a degree of fouling of the surface of the test sample.
2. The evaluation method of fouling according to claim 1, wherein a degree of recovery from fouling of the surface is evaluated by cleaning the surface of the test sample and evaluating the degree of fouling of the test sample again after evaluating the degree of fouling of the surface of the test sample.
3. The evaluation method of fouling according to claim 2, wherein the degree of fouling of the surface of the test sample is evaluated based on a L*a*b* color model specified by International Commission on Illumination (CIE).
4. The evaluation method of fouling according to claim 1, wherein the degree of fouling of the surface of the test sample is evaluated based on a L*a*b* color model specified by International Commission on Illumination (CIE).

* * * * *